(12) United States Patent
Niklas et al.

(10) Patent No.: US 8,330,472 B2
(45) Date of Patent: Dec. 11, 2012

(54) DEVICE AND METHOD FOR DETECTING ELECTRICAL PROPERTIES OF A SAMPLE OF AN EXCITABLE MATERIAL

(75) Inventors: Jürgen Niklas, Oberachöne (DE); Kay Dornich, Grossschirma (DE); Gunter Erfurt, Freiberg (DE)

(73) Assignee: Deutsche Solar GmbH, Freiberg (DE)

( * ) Notice: Subject to any disclaimer, the term of this patent is extended or adjusted under 35 U.S.C. 154(b) by 352 days.

(21) Appl. No.: 12/513,200

(22) PCT Filed: Oct. 13, 2007

(86) PCT No.: PCT/EP2007/008907
§ 371 (c)(1),
(2), (4) Date: Jan. 4, 2010

(87) PCT Pub. No.: WO2008/052648
PCT Pub. Date: May 8, 2008

(65) Prior Publication Data
US 2010/0141271 A1 Jun. 10, 2010

(30) Foreign Application Priority Data
Nov. 3, 2006 (DE) ...................... 10 2006 051 577.3

(51) Int. Cl.
*G01R 27/04* (2006.01)
(52) U.S. Cl. .............. 324/637; 438/10; 438/11; 438/17; 438/18
(58) Field of Classification Search .................. 438/381
See application file for complete search history.

(56) References Cited

U.S. PATENT DOCUMENTS

| 4,107,617 | A | * | 8/1978 | Tran ............................... 315/505 |
| 4,286,215 | A | | 8/1981 | Miller |
| 4,839,588 | A | * | 6/1989 | Jantsch et al. ........... 324/750.03 |
| 4,890,054 | A | | 12/1989 | Maeno et al. |
| 5,138,255 | A | * | 8/1992 | Kusama et al. .......... 324/754.06 |
| 5,438,276 | A | | 8/1995 | Kawata et al. |
| 6,100,703 | A | | 8/2000 | Davidov et al. |
| 7,432,714 | B2 | * | 10/2008 | Prins .............................. 324/322 |
| 7,550,963 | B1 | * | 6/2009 | Xiang et al. ............. 324/754.23 |
| 2003/0038633 | A1 | * | 2/2003 | Hyde et al. ..................... 324/316 |

FOREIGN PATENT DOCUMENTS
DE 34 07 850 A1 9/1985
(Continued)

OTHER PUBLICATIONS

Sumie et al., Detection of Heavy metal Contamination in Semiconductor Processes using a Carrier Lifetime Measurement System, Kobe Steel Engineering Report, vol. 52 No. 2, Sep. 2002, pp. 87-93.

*Primary Examiner* — Huy Q Phan
*Assistant Examiner* — Temilade S Rhodes-Vivour
(74) *Attorney, Agent, or Firm* — McGlew and Tuttle, P.C.

(57) ABSTRACT

A device for detecting electrical properties of a sample of an excitable material, in particular of a silicon wafer, comprises a microwave source for generating a microwave field, a resonance system which is coupled to the microwave source in a microwave-transmitting manner, the resonance system comprising a microwave resonator with at least one opening and a sample to be examined which is arranged next to the at least one opening, at least one excitation source which is arranged in the surroundings of the sample for controlled electrical excitation of the sample, and a measuring device for measuring at least one physical parameter of the resonance system.

15 Claims, 3 Drawing Sheets

FOREIGN PATENT DOCUMENTS

| | | |
|---|---|---|
| DE | 44 00 097 A1 | 7/1995 |
| EP | 0 155 225 B1 | 6/1991 |
| JP | H11-312719 A | 11/1999 |
| JP | 2002-228600 A | 8/2002 |
| JP | 20060196621 A | 7/2006 |
| WO | WO 92/11528 | 7/1992 |

* cited by examiner

DEVICE AND METHOD FOR DETECTING ELECTRICAL PROPERTIES OF A SAMPLE OF AN EXCITABLE MATERIAL

CROSS REFERENCE TO RELATED APPLICATIONS

This application is a United States National Phase application of International Application PCT/EP2007/008907 and claims the benefit of priority under 35 U.S.C. §119 of German Patent Application DE 10 2006 051 577.3 filed Nov. 3, 2006, the entire contents of which are incorporated herein by reference.

FIELD OF THE INVENTION

The invention relates to a device for detecting electrical properties of a sample of an excitable material. The invention further relates to a method for detecting electrical properties of a sample of an excitable material.

BACKGROUND OF THE INVENTION

The photoconductivity of semiconductors has been known for approximately half a century. In this effect, free charge carriers are generated in a semiconductor by irradiation of light. The precise details of this process are material-dependent. Furthermore, even the smallest irregularities in the crystal structure of a semiconductor may lead to huge differences in terms of the number and the electrical properties, such as mobility and lifetime, of the charge carriers that are generated. Inhomogeneities of this type have a negative effect on the quality of semiconductor components such as wafers. It is therefore of greatest interest to provide a detailed topography of the electrical properties of a wafer to detect crystal defects, particularly as early as during the production of the wafer. This may take place on the basis of the interaction of the optically generated charge carriers with an external microwave field.

DE 44 00 097 A1 describes a method in which the surface of a semiconductor material to be measured is exposed to light which excites charge carriers on the thin surface layer of the semiconductor material. An electromagnetic wave projected onto the surface of the semiconductor material is reflected by the surface to an extent which varies depending on the current charge carrier density. The reflected wave is detected and evaluated by a signal processing circuit.

The prior-art methods have the disadvantage of a relatively low detection sensitivity, with the result that they require unrealistically high injection rates for the use of the semiconductor components and need a long time to determine the detailed topography of an entire wafer.

SUMMARY OF THE INVENTION

It is the object of the invention to provide a method and a device which allow the detailed topography of a wafer to be determined in a short time with low injection rates.

This object is achieved by a device for detecting electrical properties of a sample of an excitable material, the device comprising:
a. a microwave source for generating a microwave field;
b. a resonance system which is coupled to the microwave source in a microwave-transmitting manner, the resonance system comprising
  i. a microwave resonator;
  ii. a sample to be examined;
c. at least one excitation source arranged in the surroundings of the sample for controlled electrical excitation of the sample; and
d. a measuring device for measuring at least one physical parameter of the resonance system.

The gist of the invention is that at least a portion of the sample to be examined serves as a partial element of a resonance system, and that an impedance change of the resonance system induced by controlled excitation of the sample is measured in a time-resolved manner. Compared to the prior art, this results in a much higher detection sensitivity while requiring much less time.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
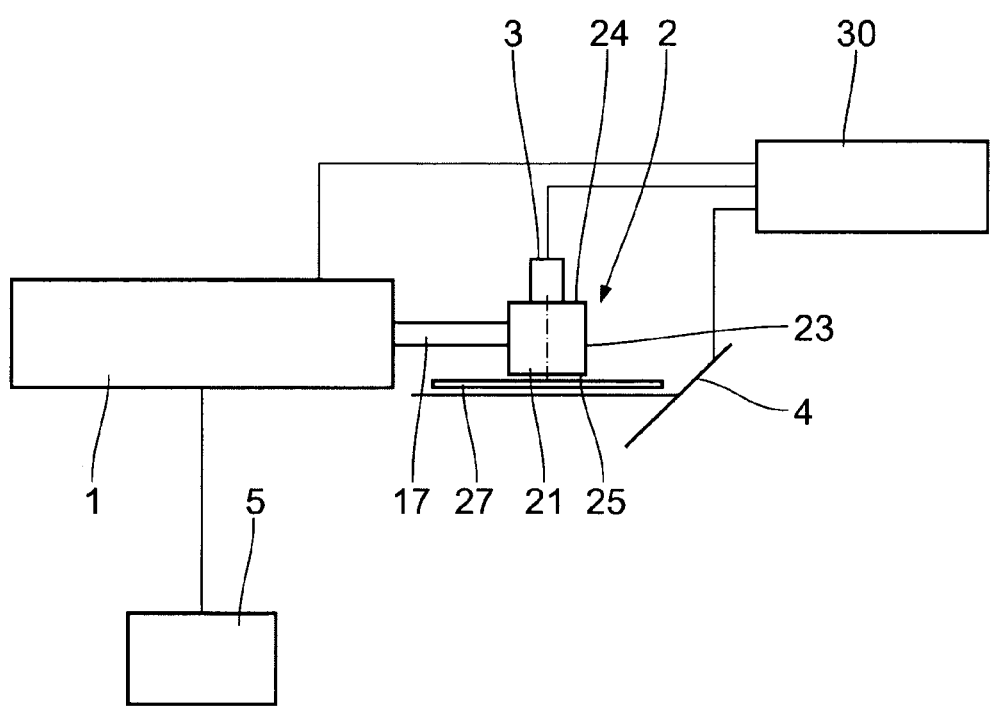
FIG. 1 is a diagrammatic view of a device according to an embodiment.

The following is a description of the layout of the device with reference to FIG. 1. A device for detecting electrical properties of a sample of an excitable material comprises a microwave bridge 1, a resonance system 2, at least one excitation source 3, a positioning device 4 and a measuring device 5. Furthermore, there may be provided a temperature control system, which is not shown in FIG. 1, for reducing or increasing the temperature of the resonance system 2. Moreover, there may be provided a device, which is not shown in FIG. 1 either, for evacuating the resonance system 2.

Figure 2:
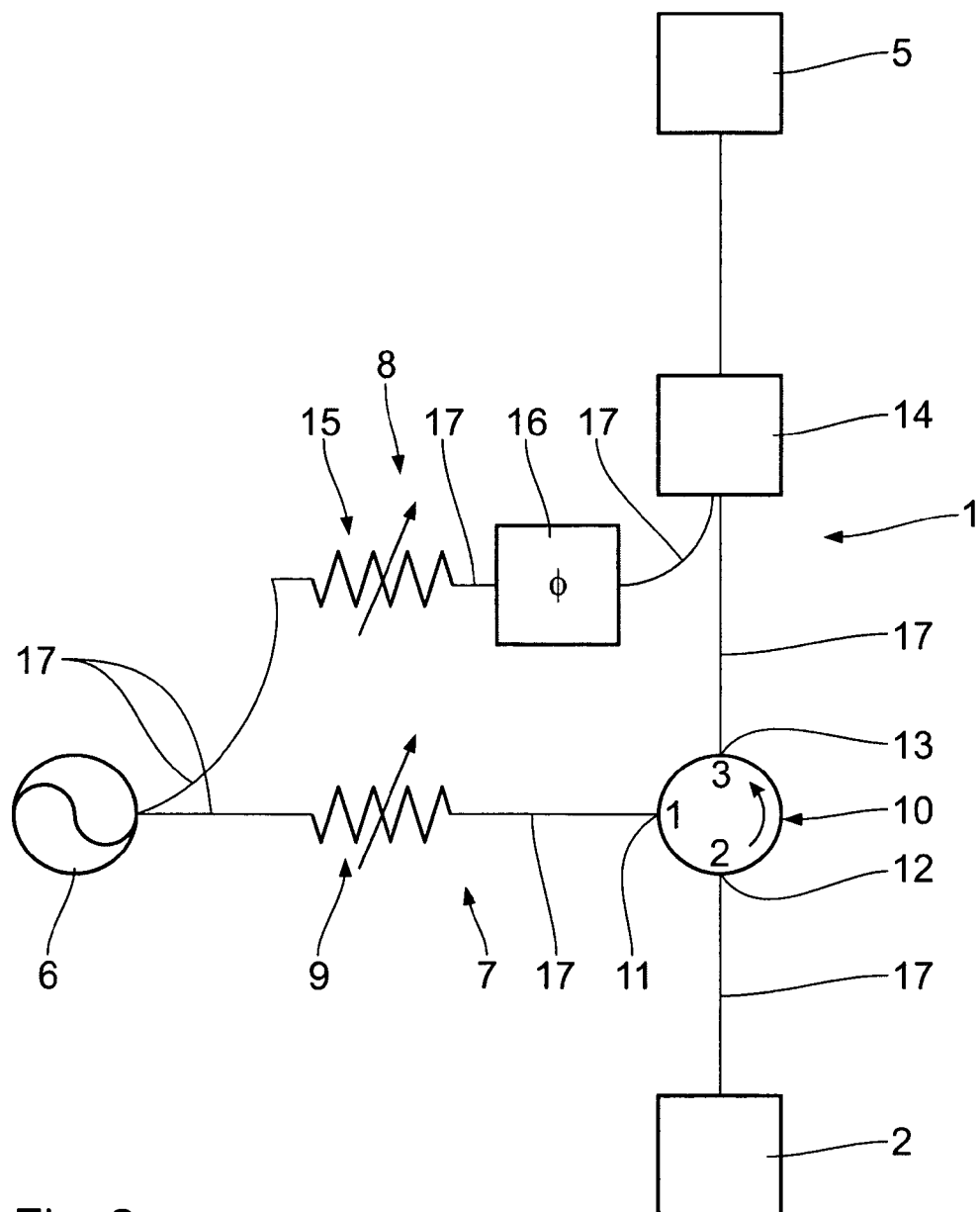
FIG. 2 is a diagrammatic view of a microwave bridge together with a resonance system and a measuring device coupled thereto.

The following is a more detailed description of the microwave bridge 1, which is known per se, with reference to FIG. 2. The microwave bridge 1 comprises a microwave source 6 which may for instance be a Gunn diode. The microwave source 6 generates microwaves in the range of 0.1 to 300 GHz, in particular in the range of 1 to 100 GHz, in particular in the range of 6 to 11 GHz, in other words in the X band. The frequency of the microwaves generated by the microwave source 6 is tunable. The microwaves are distributed to a main arm 7 and a reference arm 8 by means of a splitter which is not shown in more detail. In the main arm 7 is provided a first damper 9. A circulator 10 is provided between the first damper 9 and the resonance system 2 coupled to the microwave bridge 1, with a first arm 11 of the circulator 10 being connected to the first damper 9. A second arm 12 of the circulator 10 is connected to the resonance system 2. Finally, a third arm 13 of the circulator 10 is connected to a mixer 14. The reference arm 8 comprises a second damper 15 and a phase shifter 16. The reference arm 8 is connected to the mixer 14 as well. The connections in the microwave bridge 1 are waveguides 17, in other words they are able to transmit microwaves. They may for instance be designed as hollow guides or coaxial cables. The microwave bridge 1 may also be equipped with only one damper or no damper at all.

Figure 3:
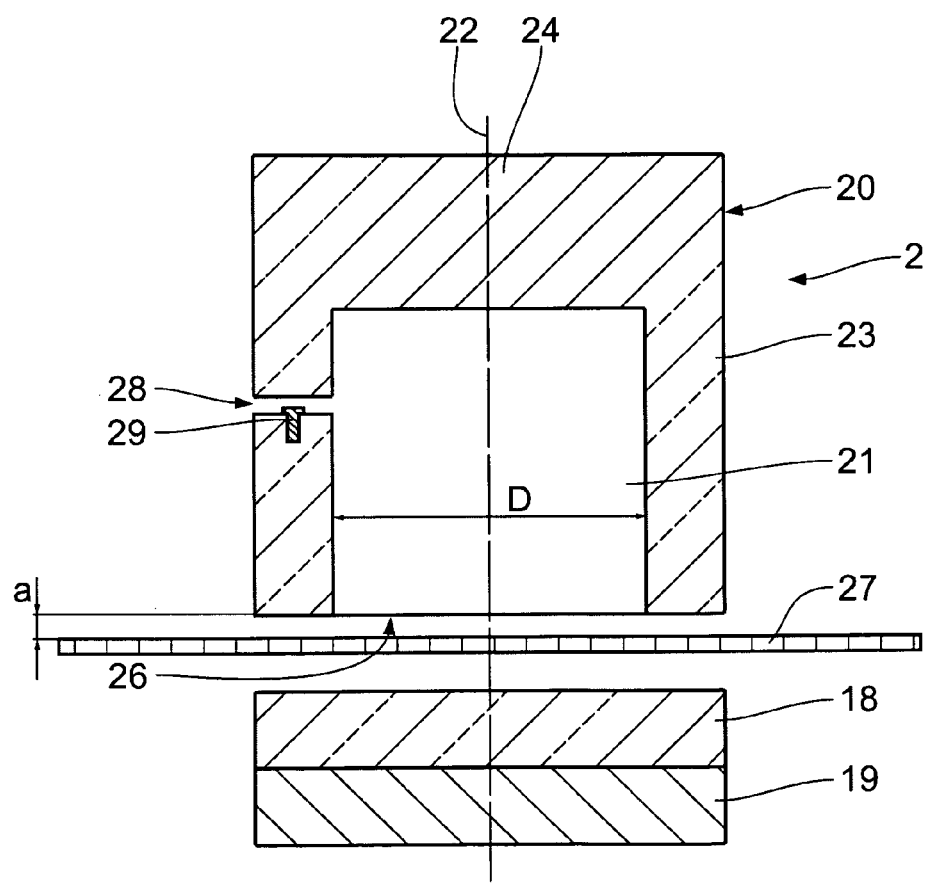
FIG. 3 is a detailed view of the resonance system.

The following is a description of the resonance system 2 with reference to FIG. 3. The resonance system 2 comprises a microwave resonator, a sample to be examined, a microwave-absorbing dielectric 18 and a microwave reflector 19. The dielectric 18 may for instance consist of glass, Teflon or air. The microwave reflector 19 consists of a material with a high electrical conductivity, for instance a metal, in particular Cu, Au, Al, brass, etc, or a highly-doped semiconductor material. It is conceivable to provide more than one microwave resonator for one sample. The microwave resonator is a cavity resonator 20, in particular a cylindrical cavity resonator 20. Other geometries of the cavity resonator 20 are conceivable as well. The cavity resonator 20 may for instance also have a cuboidal shape. The cavity resonator 20 has a quality Q, with Q>100, in particular Q>1.000.

The cylindrical cavity resonator 20 comprises a cylindrical cavity 21 with a central longitudinal axis 22, and a side wall 23 enclosing a periphery of the cavity 21 as well as at least one first front wall 24 which covers a front side of the cavity 21. A second front wall 25 is provided on the side of the cavity 21 opposite to the first front wall 24 along the central longitudinal axis 22. The second front wall 25 comprises an opening 26. The opening 26 advantageously has a circular cross-section with a diameter D and is arranged concentrically to the central longitudinal axis 22, with 1 mm<D<30 cm, in particular 1 cm<D<10 cm. The walls 23, 24, 25 defining the cavity 21 consist of a material with a high electrical conductivity, for instance a metal, in particular Cu, Au, Al, brass, etc. Along the central longitudinal axis 22, a sample to be examined is arranged outside the cavity 21 at a distance a in front of the opening 26, with a<5 cm, in particular a<1 cm, in particular a<1 mm. The greater the distance a, the lower the quality Q. The sample consists of an excitable material, in particular a semiconductor material. The sample may for instance be a wafer 27, in particular of silicon. The microwave-absorbing dielectric 18 and the microwave reflector 19 are arranged on the side of the wafer 27 opposite to the cavity resonator 20. Both the dielectric 18 and the microwave reflector 19 have dimensions perpendicular to the central longitudinal axis 22 which are at least identical to the opening 26 so that both the dielectric 18 and the microwave reflector 19 completely cover the opening 26 during a projection in the direction of the central longitudinal axis 22. Both the dielectric 18 and the microwave reflector 19 have a substantially flat shape. The dielectric 18 has a thickness in the range of 0 cm to 5 cm. The microwave reflector 19 has a thickness which is greater than the microwave skin depth, in particular greater than 10 µm. The microwave reflector 19 may also be a part of the wafer 27 itself, in particular if highly-doped material or finished solar cells are measured. Alternatively, the resonance system 2 comprises no dielectric 18.

The cavity resonator 20 comprises an iris 28 in the side wall 23. Furthermore, a tuning screw 29 is provided which is screwable into the free opening of the iris 28. Via the iris 28, the cavity resonator 20 is coupled to the microwave bridge 1 by means of one of the waveguides 17. Alternatively, the iris 28 may also be provided in the first front wall 24. Instead of the iris 28, an antenna system may be provided for coupling the microwaves of the microwave bridge 1 to the cavity resonator 20.

The entire resonance system 2 has an impedance Z which depends on the impedance of the cavity resonator 20 on the one hand and on that of the wafer 27 on the other. According to the embodiment, it is provided for several excitation sources 3 to be arranged in the surroundings of the wafer 27. This comprises all arrangements where the excitation sources 3 are able to generate free charge carriers in the wafer 27. The excitation sources 3 are in particular optical excitation sources 3, for instance lasers or LEDs. The wavelength of the light emitted by the excitation source 3 is in the range of 200 nm to 10.000 nm, in particular in the range of 400 nm to 1.200 nm. If necessary, each of the excitation sources 3 may be provided with an optical system, which is not shown in the Figures, for focussing, controlling the intensity of, and orienting the excitation. The number of excitation sources 3 is in the range of 1 to 1.000.

The excitation sources 3 are advantageously placed and oriented in such a way that the configuration of all areas on the wafer 27, which are excitable by means of the excitation sources 3, is such as to cover the wafer 27 completely while it passes into itself when rotated through an angle of 60° or 90° about the central longitudinal axis 22.

It is furthermore provided for the wafer 27 to be mounted for displacement in the plane perpendicular to the central longitudinal axis 22 by means of the positioning device 4. Alternatively, the wafer 27 may be stationary while the cavity resonator 20 is mounted for displacement in the plane perpendicular to the central longitudinal axis 22, with the dielectric 18 and the microwave reflector 19 covering the opening 26 completely even after a displacement of the cavity resonator 20. The positioning device 4 may be a robot, wafer handler, conveyor belts, etc. The microwave reflector and the dielectric may generally also be moved together with the resonator.

The microwave bridge 1, the at least one excitation source 3 and the positioning device 4 are connected to a programmable control device 30.

The following is a description of the functioning of the device according to the invention. The electrical properties of the wafer 27 to be examined are determined by means of microwaves emitted by the microwave source 6 which are coupled to the resonance system 2 via the waveguide 17 in the main arm 7 of the microwave bridge 1, and once they have passed through the circulator 10, via the iris 28. In the cavity resonator 20, the microwaves are reflected by the side wall 23 and by the first and second front walls 24, 25 substantially without losses. In the region of the opening 26 in the second front wall 25 of the cavity resonator 20, the microwaves hit the wafer 27, and in case the wafer 27 does not completely cover the opening 26, the dielectric 18 as well as the microwave reflector 19. The microwaves hitting the wafer 27 are reflected by the wafer 27 depending on the conductivity of the wafer 27. If the wafer 27 only has a low conductivity and/or does not completely cover the opening 26, then the microwaves leaving the cavity 21 via the opening 26 are reflected by the microwave reflector 19. The cavity 21 is therefore, irrespective of the conductivity of the wafer 27, completely enclosed by walls having a high conductivity, in other words it is electrically shielded. The arrangement of the wafer 27, microwave-absorbing dielectric 18 and microwave reflector 19 relative to the cavity resonator 20, in particular relative to the opening 26, proves to be all-purpose with respect to the materials to be examined. The arrangement enables the probing of wafers 27 having a low electrical conductivity as well as of those having a high electrical conductivity, and functions well even if the wafer 27 only covers a part of the opening 26.

If the microwaves coupled to the resonance system 2 have a suitable frequency, the resonance case occurs which leads to the formation of standing microwaves in the cavity 21. The wavelength and frequency of this standing microwave depend, among other things, on the geometry of the cavity 21, and in particular on the conductivity of the walls enclosing the cavity 21 as well as on the conductivity of the wafer 27.

The tuning screw 29 in the iris 28, which couples microwaves emitted by the microwave source 6 to the cavity resonator 20 via the main arm 7 by means of the waveguide 17, acts as a variable capacitor which allows the impedance of the cavity resonator 20, and therefore the impedance of the resonance system 2, to be regulated. This allows the resistance of the resonance system 2 to be tuned to that of the waveguide 17 which connects the main arm 7 of the microwave bridge 1 to the cavity resonator 20, in other words the resonance system 2 can be critically coupled to the microwave bridge 1. When the resonance system 2 is critically coupled to the microwave bridge 1, the total power of the microwaves in the waveguide 17 is coupled into the resonance system 2 so that no power is reflected by the resonance system 2.

The frequency of the microwaves generated by the microwave source 6 on the one hand and the position of the tuning screw 29 in the iris 28 on the other is tuned to the impedance of the resonance system 2 as follows:

In a first step, the frequency of the microwaves generated by the microwave source 6 is tuned to the resonance system 2, in particular to the geometry of the cavity resonator 20, in such a way that a standing microwave forms in the cavity resonator 20. Afterwards, the tuning screw 29 in the iris 28 is adjusted such that the resonance system 2 is coupled substantially critically, in other words free of reflections, to the waveguide 17 connecting the circulator 10 to the resonance system 2. The substantially critical coupling may alternatively also be achieved by exactly positioning an antenna on the inside of the cavity resonator 20. Tuning the frequency of the microwaves generated by the microwave source 6 and adjusting the tuning screw 29 may be repeated if necessary.

In the normal case, it is almost impossible for the resonance system 2 to be coupled to the microwave bridge 1 completely free of reflections. This is accounted for by adjusting the amplitude and phase of the microwaves in the reference arm 8 of the microwave bridge 1 by means of the second damper 15 and/or the phase shifter 16 in such a way that upon superimposition in the mixer 14, they cancel out the microwaves reflected by the resonance system 2 which are guided from the circulator 10 to the mixer 14 via the third arm 13. In this state, it is impossible for a signal to be transmitted from the mixer 14 to the measuring device 5.

When the at least one excitation source 3 is switched on, an electrical excitation occurs in a spatially limited portion of the wafer 27. The dimensions of the excited portion of the wafer 27 in the direction perpendicular to the central longitudinal axis 22 are defined by the extension of the light beam in this direction. The excited portion is in particular a region with a substantially circular diameter in the range of 1 µm to 4 cm, in particular in the range of 10 µm to 5 mm, when seen perpendicular to the central longitudinal axis 22. In the direction of the central longitudinal axis 22, the extension of the excited portion of the wafer 27 depends on the penetration depth of the light, which is emitted by the excitation source 3, into the wafer 27.

The excitation sources 3 are activated by the control device 30 in pulses, with the duration of a pulse being in the range of 1 µs to 1 s, in particular in the range of 10 to 100 µs. Furthermore, the excitation sources 3 are activated by the control device 30 in sequences with a frequency in the range of 1 Hz to 100 MHz, in particular 1 Hz to 1 MHz, in particular 1 kHz to 100 kHz.

The excitation generates free charge carriers in the wafer 27. This leads to a change in conductivity in at least a portion of an area bounding the cavity 21, which causes the reflection properties in this portion to change with respect to the microwaves. This also leads to a change in impedance of the resonance system 2 which is therefore no longer critically, in other words free of reflections, coupled to the microwave bridge 1. As the parameters of the microwave bridge 1 and those of the resonance system 2 have been tuned to each other such that the resonance system 2 is in resonance when the wafer 27 is in the non-excited state, combined with the very high quality of the cavity resonator 20, even the smallest changes in the conductivity of the wafer 27, which are induced by the excitation of the wafer 27 and lead to changes in the impedance of the wafer 27 and therefore of the entire resonance system 2, are detectable in a very sensitive manner. The power reflected by the resonance system 2 results in a microwave signal which enters the circulator 10 via the second arm 12 and passes from the circulator 10 to the mixer 14 via the third arm 13. In the mixer 14, the reflected signal is superimposed with the microwave signal from the reference arm 8 of the microwave bridge 1, the microwave signal being adjusted as described above before one of the excitation sources 3 is switched on. From the mixer 14, the signal is transmitted to the measuring device 5 where it is stored, processed and evaluated in a time-resolved manner. Even the smallest changes of the resonance properties of the resonance system 2 are detectable by means of this arrangement. This allows the excitation power of the excitation source 3 to be reduced down to 0.001 mW/cm$^2$. Such a low excitation power is advantageous because it is in the range of the excitation power which actually occurs during the subsequent use of the wafer. Higher excitation powers of up to approximately 100 W/cm$^2$ are conceivable as well.

The excitation sources 3 are activated in sequences by the control device 30. The time interval between switching off the preceding excitation source 3 and switching on the subsequent excitation source 3 is in the range of 1 µs to 1 s. This interval is in particular selected in such a way that more than 90%, in particular more than 99%, of the charge carriers generated when the preceding excitation source 3 is switched on have recombined as soon as the subsequent excitation source 3 is switched on.

In order for the electrical properties to be detected across the entire region of the wafer 27, the wafer 27 is precisely displaceable relative to the opening 26 of the cavity resonator 20 in the direction perpendicular to the central longitudinal axis 22 by means of the positioning device 4.

The free charge carriers generated when the excitation source 3 is switched on only have a limited lifetime and recombine as soon as this time has expired. In this regard, it has been found that the recombination of the free charge carriers is affected by crystal defects such as imperfections, impurity atoms or traps. As a general rule, the transient after switching off the excitation source 3 can be described very well by a sum of exponential functions. The rapid decrease of the transient is a measure for the recombination lifetime. In the second, less rapidly decreasing portion of the transient, one can observe the effect of crystal defects on the charge carriers. An evaluation of the signals measured by the measuring device 5, for instance by means of the two-port method in which the signal amplitude is measured after switching off the excitation source 3 in two intervals preferably having the same length but different starting times before being subject to further evaluation, enables conclusions to be made about the distribution and concentration of crystal defects in the wafer 27 and about the diffusion length, in other words the mobility of the free charge carriers, in a simple manner.

The number of measuring points to be measured for a topography of an entire wafer depends on the required resolution, i.e. on the diameter of the light beam of the excitation sources 3, the size of the wafer 27 and the material quality; the available time has so far been another important factor. The device and the method according to the invention considerably reduce the time required for a topographic detection of the electrical properties of an entire wafer. A topographic detection of this type performed on a typical wafer using the means described herein takes less than 10 s, in particular less than 1 s.

In order to improve the signal-to-noise ratio, the measurements can be repeated several times.

While a specific embodiment of the invention have been described in detail to illustrate the application of the principles of the invention, it will be understood that the invention may be embodied otherwise without departing from such principles.

The invention claimed is:

1. A device for detecting electrical properties of a sample of an excitable material, the device comprising:
   a microwave source for generating a microwave field;
   a resonance system which is coupled to the microwave source in a microwave-transmitting manner, the resonance system comprising a microwave resonator and a sample to be examined;
   at least one excitation source arranged in the surroundings of the sample for controlled electrical excitation of the sample; and
   a measuring device for measuring at least one physical parameter of the resonance system, wherein the microwave resonator is a cavity resonator with a cavity, said cavity resonator comprising an opening, the sample being arranged in front of said opening at a position outside said cavity, wherein a microwave-absorbing dielectric is arranged on the side of the sample remote from the opening.

2. A device according to claim 1, wherein a microwave reflector is arranged on the side of the sample remote from the opening.

3. A device according to claim 1, wherein the at least one excitation source is activated pulsedly.

4. A device according to claim 1, wherein several excitation sources are provided.

5. A device according to claim 4, wherein the excitation sources are activated sequentially.

6. A device according to claim 1, wherein the sample and the cavity resonator are displaceable relative to each other in a plane perpendicular to the central longitudinal axis.

7. A device according to claim 1, wherein the sample is a silicon wafer.

8. A device for detecting electrical properties of a sample of an excitable material, the device comprising:
   a microwave source;
   a resonance system coupled to said microwave source, said resonance system comprising a microwave cavity resonator, said microwave cavity resonator comprising a side wall, at least a portion of said side wall defining a cavity of said microwave cavity resonator, said cavity comprising an opening, said resonance system comprising a sample, said sample being arranged in front of said opening at a position outside said cavity, said microwave source generating one or more microwaves such that said one or more microwaves are reflected by at least a portion of said side wall through said opening to said sample to define at least one microwave travel path;
   an excitation source for controlled electrical excitation of the sample, wherein a microwave-absorbing dielectric is arranged on one side of said sample, said resonator resonance system and said excitation source being arranged on another side of said sample; and
   a measuring device for measuring at least one physical parameter of the resonance system.

9. A device in accordance with claim 8, wherein said microwave cavity resonator comprises a first front wall, said one or more microwaves being reflected by at least a portion of said first front wall to define a portion of said at least one microwave travel path.

10. A device in accordance with claim 9, wherein said microwave cavity resonator comprises a second front wall, said one or more microwaves being reflected by at least a portion of said second front wall to define another portion of said at least one microwave travel path.

11. A device in accordance with claim 8, wherein said excitation source is activated pulsedly.

12. A device in accordance with claim 8, further comprising:
   another excitation source.

13. A device in accordance with claim 12, wherein said excitation source and said another excitation source are activated sequentially.

14. A device in accordance with claim 8, wherein the sample and the microwave cavity resonator are displaceable relative to each other in a plane perpendicular to a central longitudinal axis of said microwave cavity resonator.

15. A device for detecting electrical properties of a sample of an excitable material, the device comprising:
   a microwave source;
   a resonance system coupled to said microwave source, said resonance system comprising a microwave cavity resonator, said microwave cavity resonator comprising a side wall, at least a portion of said side wall defining a cavity of said microwave cavity resonator, said cavity comprising an opening, said resonance system comprising a sample, said sample being arranged in front of said opening at a position outside said cavity, said microwave source generating one or more microwaves such that said one or more microwaves are reflected by at least a portion of said side wall through said opening to said sample to define at least one microwave travel path;
   an excitation source for controlled electrical excitation of the sample, wherein a microwave-absorbing dielectric and a microwave reflector are arranged on one side of said sample, said resonator resonance system and said excitation source being arranged on another side of said sample; and
   a measuring device for measuring at least one physical parameter of the resonance system.

* * * * *

UNITED STATES PATENT AND TRADEMARK OFFICE
CERTIFICATE OF CORRECTION

PATENT NO. : 8,330,472 B2  
APPLICATION NO. : 12/513200  
DATED : December 11, 2012  
INVENTOR(S) : Jürgen Niklas Page 1 of 1

It is certified that error appears in the above-identified patent and that said Letters Patent is hereby corrected as shown below:

On the Title page (item 75)

The inventor Jürgen NIKLAS address is Oberschöna and not Oberschöne.

Please change Oberschöne to Oberschöna.

Signed and Sealed this  
Tenth Day of September, 2013

Teresa Stanek Rea  
*Acting Director of the United States Patent and Trademark Office*